US009222185B2

(12) United States Patent
Cornelius et al.

(10) Patent No.: US 9,222,185 B2
(45) Date of Patent: Dec. 29, 2015

(54) NANOWIRE STRUCTURAL ELEMENT

(75) Inventors: Thomas Cornelius, Grenoble (FR); Wolfgang Ensinger, Munster (DE); Reinhard Neumann, Dossenheim (DE); Markus Rauber, Darmstadt (DE)

(73) Assignee: GSI Helmholtzzentrum fur Schwerionenforschung GmbH (DE)

( * ) Notice: Subject to any disclaimer, the term of this patent is extended or adjusted under 35 U.S.C. 154(b) by 1159 days.

(21) Appl. No.: 12/933,184

(22) PCT Filed: Mar. 12, 2009

(86) PCT No.: PCT/EP2009/001776
§ 371 (c)(1),
(2), (4) Date: Dec. 9, 2010

(87) PCT Pub. No.: WO2009/115227
PCT Pub. Date: Sep. 24, 2009

(65) Prior Publication Data
US 2011/0211994 A1    Sep. 1, 2011

(30) Foreign Application Priority Data

Mar. 20, 2008   (DE) .......................... 10 2008 015 333

(51) Int. Cl.
*B82Y 15/00*   (2011.01)
*B82Y 30/00*   (2011.01)
(Continued)

(52) U.S. Cl.
CPC ............. *C25D 1/006* (2013.01); *B01J 19/0093* (2013.01); *B01J 23/42* (2013.01); *B01J 23/72* (2013.01); *B01J 35/0006* (2013.01); *B22F 1/0025* (2013.01); *B22F 3/002* (2013.01);
(Continued)

(58) Field of Classification Search
CPC ......... B82Y 15/00; B82Y 30/00; B82Y 40/00
See application file for complete search history.

(56) References Cited

U.S. PATENT DOCUMENTS

| 5,449,917 A | 9/1995 | Clements |
| 5,911,863 A | 6/1999 | Vetter et al. |

(Continued)

FOREIGN PATENT DOCUMENTS

| EP | 1884578 A1 | 2/2008 |
| JP | 2004207448 A | 7/2004 |

(Continued)

OTHER PUBLICATIONS

D. Wang et al., A General Route to Macroscopic Hierarchical 3D Nanowire Networks, 43 Angew. Chem. Int. Ed. 6169-6173 (2004)).*

(Continued)

*Primary Examiner* — Randy Boyer
(74) *Attorney, Agent, or Firm* — Reising Ethington PC

(57) ABSTRACT

The invention concerns a nanowire structural element suited for use in a microreactor system or microcatalyzer system. A template based process is used for the production of the nanowire structural element, wherein the nanowires are electrochemically depositioned in the nanopores. The irradiation is carried out at different angles, such that a nanowire network is formed. The hollow chamber-like structure in the nanowire network is established through the dissolving of the template foil and removal of the dissolved template material. The interconnecting of the nanowires provides stability to the nanowire structural element and an electrical connection between the nanowires is created thereby.

12 Claims, 6 Drawing Sheets

Figure 1:
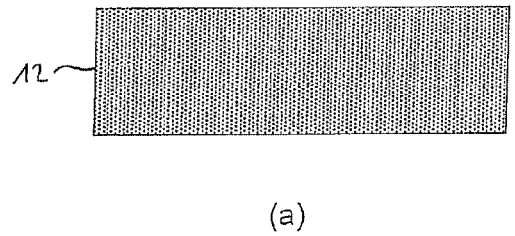
Figure 1:
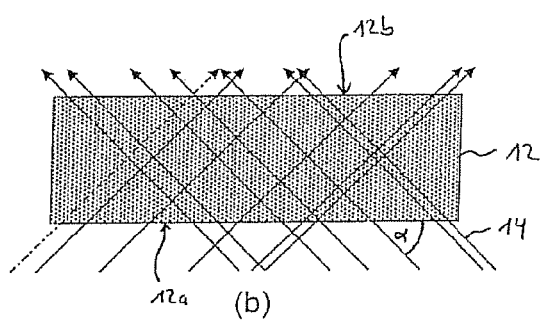
Figure 1:
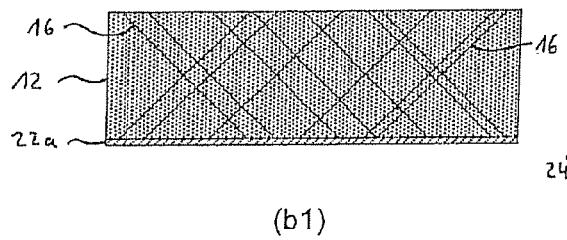
Figure 1:
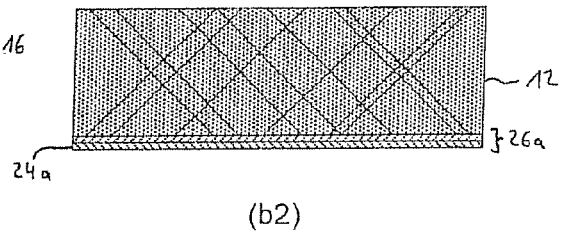
Figure 1:
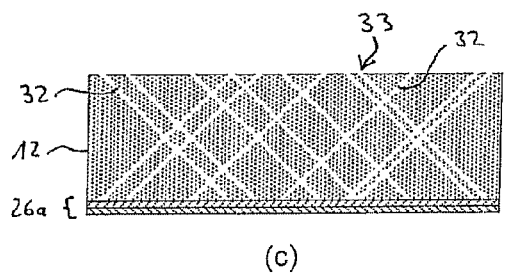
Figure 1:
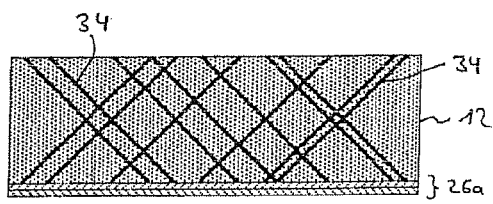
Figure 1:
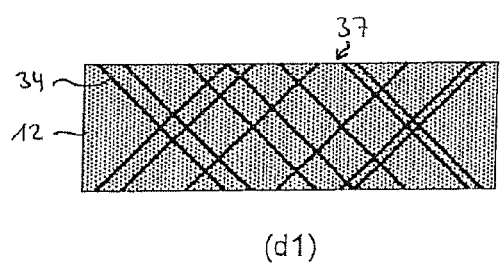
Figure 1:
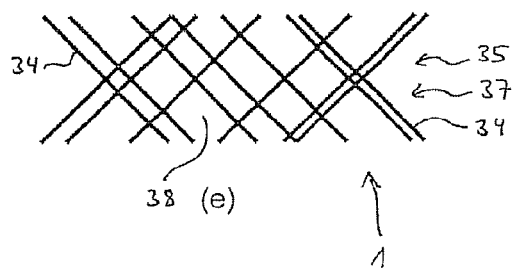

(51) Int. Cl.

| | |
|---|---|
| B82Y 40/00 | (2011.01) |
| C25D 1/00 | (2006.01) |
| B01J 19/00 | (2006.01) |
| B01J 23/42 | (2006.01) |
| B01J 23/72 | (2006.01) |
| B01J 35/00 | (2006.01) |
| B22F 1/00 | (2006.01) |
| B22F 3/00 | (2006.01) |
| B81C 99/00 | (2010.01) |
| C25D 1/04 | (2006.01) |
| C25D 1/08 | (2006.01) |
| C25D 5/18 | (2006.01) |

(52) U.S. Cl.
CPC ............. *B81C99/0085* (2013.01); *B82Y 15/00* (2013.01); *B82Y 30/00* (2013.01); *C25D 1/00* (2013.01); *C25D 1/003* (2013.01); *C25D 1/04* (2013.01); *C25D 1/08* (2013.01); *B01J 2219/0086* (2013.01); *B01J 2219/00783* (2013.01); *B01J 2219/00835* (2013.01); *B01J 2219/00846* (2013.01); *B01J 2219/00853* (2013.01); *B01J 2219/00873* (2013.01); *B81B 2201/0292* (2013.01); *B81B 2201/051* (2013.01); *B82Y 40/00* (2013.01); *C25D 5/18* (2013.01); *Y10S 977/762* (2013.01); *Y10T 29/49117* (2015.01); *Y10T 428/12201* (2015.01); *Y10T 428/24562* (2015.01); *Y10T 428/25* (2015.01)

(56) References Cited

U.S. PATENT DOCUMENTS

| | | | |
|---|---|---|---|
| 6,033,583 | A | 3/2000 | Musket et al. |
| 6,328,342 | B1 | 12/2001 | Belousov et al. |
| 2005/0230353 | A1 | 10/2005 | Danziger |
| 2006/0124467 | A1 | 6/2006 | Ho et al. |
| 2006/0134392 | A1 | 6/2006 | Hantschel et al. |
| 2008/0036038 | A1 | 2/2008 | Hersee et al. |

FOREIGN PATENT DOCUMENTS

| | | |
|---|---|---|
| WO | WO 2009/115230 | 9/2009 |
| WO | WO 2010/029550 | 3/2010 |

OTHER PUBLICATIONS

S. Valizadeh et al., Electrochemical Synthesis of Ag/Co Multilayered Nanowires in Porous Polycarbonate Membranes, Thin Solid Films 402, pp. 262-271 (2002).

I.U. Schuchert et al., "Electrochemical Copper Deposition in Etched Ion Track Membranes", Journal of the Electrochemical Society 150 (4) pp. C189-C194 (2003).

M.E. Toimil Molares et al., "Fabrication and Contacting of Single Bi Nanowires", Nanotechnology 15, pp. S201-S207 (2004).

Changwei Xu et al., "Highly Ordered Pd Nanowire Arrays as Effective Electrocatalysts for Ethanol Oxidation in Direct Alcohol Fuel Cells", Adv. Mater. 2007, 19, pp. 4256-4259.

Japanese Office Action Re: Application No. 2011-500077 Dated: Oct. 18, 2013.

Wang, D. et al: "A General Route to Macroscopic Hierarchical 3DNanowire Networks" Angewandle Chemie International Edition, Bd. 43, Nr. 45 Nov. 17, 2004 XP002547982.

Gu, Z. et al:Three Dimensional Electrically Interconnected Nanowire Networks Formed by Diffusion Bonding Langmuir Bd. 23, Nr. 3, Dec. 23, 2006, Seiten 979-982 XP002547983.

Lindeberg, M.; Hjort K: "Interconnected nanowire clusters in polyiminde for flexible circuits and magnetic sensing applications" Sensors and Actuators A, XP004428584.

Lui, J et al: Electrochemical fabricationof single-crystalline and polycrystalline Au nanowires: the influence of deposition parameters Nanotechnology, IOP, Bristol, GB.

Mukherji, D. et al: Nano-structured materials produced from simple metallic alloys by phase separation; Nanotechnology, IOP, Bristol, GB XP020090762.

Linberg, M.; Hjort K: "A comprehensive study of ion track enabled high aspect ration microstructures in flexible circuit boards" Microsystem Technologies, Berlin, DE Bd. 10.

Ursache Andrei; Goldbach James; Russell Thomas; Tuominen Mark: Pulse electrodeposition and eletrochemical quartz crystal microbalance techniques for high perpindicular magneti.

Yi-Kun, Su, et al: Microstructure and Magnetic Properties of Bamboo-like . . . Chemical Physics Letters, Bd. 388, Nr.4-6 Apr. 21, 2004 Seiten 406-418 XP002547633.

Maurer, Florin, et al:"Preferred growth orientation of metallic fcc nanowires under direct and alternating electrodeposition conditions" Nanotechnology 18, pp. 135709 (2007).

Karim, S., et al:"Tuning the Characteristics of Electrochemically Fabricated Gold Nanowires" J.Nanosc.Nanotechnol.8, pp. 5659-5666 (2008).

Karim, S., et al:"Synthesis of gold nanowires with controlled crystallographic characteristics" App. Phys. A 84, pp. 403-407 (2006).

* cited by examiner (a)

(b)

(b1)

(b2)

(c)

(d)

(d1)

(e)

NANOWIRE STRUCTURAL ELEMENT

FIELD OF THE INVENTION

The invention concerns a nanowire structural element, a process for production of said and a micro-reactor system, specifically a microcatalyzer system.

BACKGROUND OF THE INVENTION

In "Chemistry in Microstructured Reactors," Ang. Chem. Int. Ed. 2004, 43, 406-466 [: Applied Chemistry, International Edition], K. Jähnisch et al. have demonstrated the advantages that microstructured components have in chemical reactions and for analytical purposes. This has led to an increase in the importance that such systems have for chemical synthesis and analysis. In comparison to conventional reactors, these microstructures have a large surface area/volume ratio, which has a positive influence on the transference of heat as well as the process of the transportation of matter (see also: O. Wörz et al. "Micro-reactors—A New Efficient Tool for Reactor Development," Chem. Eng. Technol. 2001, 24, 138-142).

Many known reactions have been carried out in microstructure reactors, including many catalytic reactions. For these, it is unimportant whether the reactions are liquid phase, gas phase or gas-liquid phase reactions. In order to take advantage of the potential activity of the catalyzer, the catalytic material is integrated in microstructured systems with various geometric forms. In the simplest case, the reaction material used for the construction of the micro-reactor consists in itself of the catalytically active substance (see also: M. Ficthner, "Microstructured Rhodium Catalysts for the Partial Oxidation of Methane to Syngas under Pressure," Ind. Eng. Chem. Res. 2001, 40, 3475-3483). This means however that the catalytic surface is limited to the walls of the reactor. This disadvantage is partially resolved by means of optimized catalyzer/carrier systems. For the most part, current microstructure reactors contain small particles or powder, which are incorporated in a channel.

Catalyzer filaments, wires and membranes are also used however (see also: G. Veser, "Experimental and Theoretical Investigation of $H_2$ Oxidation in a High-Temperature Catalytic Microreactor," Chem. Eng. Sci. 2001, 56, 1265-1273). Metallic nanostructures, particularly those from transition metals, are known in heterogenic catalysis due to their high ratio of surface area/mass, resulting in lower production costs (see also: R. Narayanan et al. "Catalysis with Transition Metal Nanoparticles in Colloidal Solution: Nanoparticle Shape Dependence and Stability," J. Chem. Phys. B, 2005, 109, 12633-12676).

Originally, research was concentrated on the examination of isotropic metal particles, and as a result, their catalytic characteristics have been studied at length. At present, however, many one-dimensional nanostructures have been analyzed regarding their use in heterogenic catalysis. The stabilization of these is a major problem. The incorporation of nanostructures on a carrier or storage of them in porous matter such as, e.g. Nafion is known from Z. Chen et al. "Supportless Pt and PtPd Nanotubes as Electrocatalysts for Oxygen-Reduction Reactions," Ang. Chem. 2007, 119, p. 4138-4141, which leads however directly to a decrease in the utilizable catalyzer surface area. Furthermore, it must be noted that the catalytic activity is dependent on the distribution of the catalyzer material due to the diffusion processes. Accordingly, the nanoparticles significantly increase the surface area/volume ratio, but long-term stability of such reactors is relatively limited due to the following:

1. Loss of contact between nanoparticles due to corrosion of the carrier.
2. Dissolving and renewed deposition or Ostwald ripening.
3. Aggregation of the nanoparticles in order to minimize the surface energy.
4. Dissolving of the nanoparticles and migration of the dissolvable ions.

Parallel wire and tube structures have already been used as glucose sensors (J. H. Yuan et al., "Highly Ordered Platinum-Nanotubule Arrays for Amperometric Glucose Sensing," Adv. Funct. Mater. 2005, 15, 803), as electrocatalysts, for example, in alcohol oxidation (H. Wang et al., "Pd Nanowire Arrays as Electrocatalysts for Ethanol Electrooxidation," Electrochem. Commun. 2007, 9, 1212-1216) and for hydrogen peroxide reduction (H. M. Zhang et al., "Novel Electrocatalytic Activity in Layered Ni—Cu Nanowire Arrays," Chem. Cornimm. 2003, 3022). In these cases however, the nanostructures are not particularly stable.

Nielsch et al. have reported in "Uniform Nickel Deposition into Ordered Alumina Pores by Pulsed Electrodeposition," Adv. Mater. 2000, 12, 582-586, that pulsed deposition is used for deposition of thin metallic foils.

A process for the generation of nanowires known from, for example, T. W. Cornelius et al., "Controlled Fabrication of Poly- and Single-Crystalline Bismuth Nanowires," Nanotechnology 2005, 16, p. 246-249; or from the dissertations by Thomas Walter Cornelius, GSI, 2006; Florian Maurer, GSI, 2007 and Shafgat Karim, GSI, 2007, which are hereby incorporated as references. With these processes however, only single nanowires were obtained.

GENERAL DESCRIPTION OF THE INVENTION

The invention has the object of providing a complex nanowire structural element and a process for the production of said which has a stable hollow chamber-like structure with a large specific surface area.

A further object of the invention is to provide a nanowire structural element of this type which may be used in a number of ways, e.g. as a catalytic element.

The object of the invention is achieved by means of the object of the independent claims. Advantageous embodiments of the invention are defined in the dependent claims.

A process is provided for the production of a nanowire structural element which contains a nanowire array of numerous nanowires, wherein the nanowires run in different directions and the nanowires running in different directions intersect, thereby forming a meshed network of nanowires. The meshed network forms, thereby, an open cell hollow chamber-like structure with a very large interaction surface area. The hollow chamber-like structure may be envisioned as a chamber that can be open at one or more edges.

For production a so-called template based process is used as follows.

In a first process step (a), first, a dielectric template, in particular a dielectric template foil, is prepared. The template foil is, for example, a conventional commercially available synthetic foil, in particular, a polymer foil.

In a subsequent process step (b) the template foil is irradiated (c1) with high-energy radiation, in particular with a highly energetic ion radiation, such as is available, for example, in the accelerator facility of the Gesellschaft far Schwerionenforschtmg mbH [: Center for Heavy Ion Research; abbreviation: GSI] in Darmstadt. As a result of the irradiation a large number of latent tracks permeate the template foil. The tracks are characterized in that the molecular structure, e.g. the polymer structure of the foil is corrupted along the trajectory of each irradiation ion. These tracks are referred to as "latent tracks." The damage is greatest at the core of the track and is $1/r^2$. Using etching techniques, the material having a corrupted molecular structure can be removed from the track and the latent track becomes by this means an open channel, or respectively, a so-called nanopore can be etched. The latent tracks and thereby the subsequently generated nanopores are stochastically distributed in relation to the plane of the template surface.

In accordance with the invention, the template, or respectively, the template foil in step (b) is irradiated from at least two, preferably three or more, angles to the surface of the template—in other words, from at least two, preferably three or more different directions. In this manner latent tracks are first created in the template foil that run in at least two, preferably three or more different, non-parallel directions. For example, a polycarbonate foil is irradiated with heavy ions having an energy ranging from a few to a few tens MeV/u at two angles (+45°, −45°) in relation to the surface plane of the template foil.

Particularly preferable thereby is that the template foil is irradiated from at least three (or more) different directions which are not in the same plane, wherein a three-dimensional interconnected nanopore network can be produced, which will be explained in greater detail in the following. For example, a polycarbonate foil is irradiated with heavy ions having an energy of a few to a few hundred MeV/u from three different directions, e.g. at a polar angle in each case of 45° to the surface plane and with an azimuth angle at 0°, 120° and 240° to the surface plane with a fluence of a few $10^8$ ions/cm² in each case. It is clear that the complexity of the network can be increased through more irradiation angles. In this case, the energy of the ions is selected such that said fully penetrate the foil. The energy of the ion beam is thereby dependent on the thickness of the foil which is to be irradiated.

Preferably, an electroconductive metallic layer as, if applicable, a temporary, cathode layer is applied to the first side of the template foil and this, preferably after the ion irradiation has been carried out, and further preferably before etching, but at least prior to the electrochemical deposition. Preferably, therefore, the nanopores are etched from the latent ion induced tracks after the cathode layer is at least partially applied to the template foil. In this manner, material from the cathode layer being depositioned in the pores is avoided. Furthermore, the pores are particularly strictly cylindrical and do not taper at either end.

Preferably, for the production of the cathode layer, first a thin metal layer is applied to the first side of the template foil, e.g. a gold layer is sputtered onto said, and subsequently this gold layer is reinforced with, for example, a copper layer. This has the advantage that first a relatively thin layer can be sputtered.

In the process step (c) the template foil is subjected to an etching procedure wherein the latent tracks in the template foil are enlarged to form continuous channels which fully penetrate the template foil, thereby reaching from one surface of the template foil to the opposite surface of the template foil. These channels are referred to in the field as nanopores. At the beginning of the etching procedure the most corrupted part of the molecular structure at the track core is dissolved away and with increasing etching periods the diameter of the nanopores is increased. Due to the irradiation of the template foil from different directions and the resulting intersecting network of latent tracks, a network of intersecting nanopores is formed through etching. The intersecting nanopores are so densely arranged that a significant portion of the intersecting nanopores are interconnected such that an interconnected channel system with numerous branches is formed. When irradiation is carried out from at least three directions not lying in a common plane, a three-dimensional interconnected channel system of nanopores is formed.

In a subsequent step (d), starting at the inner side of the cathode layer, nanowires are grown in the nanopores within the template foil by means of electrochemical deposition, i.e. the nanopores are filled by the cathode layer by means of electrochemical deposition, wherein the nanowires grow in the nanopores. For this purpose, the dielectric foil, permeated with pores and electroconductively coated on one side, is placed in an electrochemical deposition device, wherein the cathode layer serves as a cathode for the electrochemical deposition procedure of the nanowires. The nanowires are grown in the nanopores from metal ions by means of electrochemical deposition, wherein the metallic nanowires develop inside the nanopores, in particular, directly on the cathode layer and are thereby integrally joined to the cathode layer by reason of being grown together. The cathode layer may remain as a substrate layer firmly joined to the individual nanowires of the nanowire structural element to be generated, but may also, if desired, be removed after the generation of the nanowire network. In the meshed network of nanopores or nanochannels, a meshed network of intersecting nanowires is formed thereby. At the nodes at which the nanopores are interconnected, nodes in the nanowire network are formed accordingly, at which the intersecting metal nanowires grow together, or respectively, become integrally joined with each other. In this manner an integrated network of intersecting nanowires joined together can be generated. The template foil at this point of the process is permeated by the connected network of intersecting and interconnected nanowires in the manner of reinforced concrete.

The nanowires develop therefore inside the nanopores in the template foil in at least two, at least three, or more, predefined different directions which are determined by the direction of the irradiation. If the irradiation is carried out from at least three directions which do not lie in a common plane, then the nanowires in the network run along at least three predefined different directions which are not in a common plane, thus producing a three-dimensional interconnected nanowire network. In a three-dimensional interconnected nanowire network, the nanowires of a first of the, at least three, predefined directions accordingly are connected to other nanowires of not only a second predefined direction but also with nanowires of at least one third direction, wherein the third direction does not lie in the planes through which the first and second directions run.

When the network of nanowires is completely depositioned, or respectively, matured, the template foil is dissolved, in particular by chemical means, in a step (e) and the network of nanowires is thereby exposed. The template foil is reduced in the dissolving to such small components that these components can be removed from the space permeated by the nanowire network without damaging the nanowire network. If the template foil is a synthetic foil, this can, for example, be dissolved with a solvent. Due to the meshing of the network, or respectively, the integral joining of the intersecting nanowires, the integrally joined nanowire network has an inherent stability even after the removal of the template foil, and this with only one cover layer (cathode/substrate layer) and, if applicable, even without a cover layer. The joined network of nanowires forms an open cell hollow chamber-like structure which is at least inherently stable, which can be handled, carefully, relatively well.

This means that in accordance with the invention, the cathode layer can even be fully removed after the network of nanowires is fully depositioned, or respectively, formed, if desired. The cathode layer is then, in particular, removed from the template foil after the deposition of the nanowire network and prior to the dissolving and removing of the template foil. This is, for example, particularly possible when the cathode layer and the nanowire network are of different metals where they meet. The removal of the cathode layer is however not necessary, and can remain integrally joined to the nanowire network if, for example, a closed cover layer integrally joined to the nanowire network is desired. If the cathode layer remains on the nanowire network, it forms a substrate layer which also increases the stability and makes the nanowire structural element easier to handle. Preferably, the nanowire structural element forms thereby a flat mat-like shape. In particular, it is also possible to produce a flat nanowire structural element, which on at least one flat side of the nanowire network does not have a cover layer, and is therefore open and the opposite flat side of the nanowire network is firmly joined to the substrate layer, or respectively, unified with said. In this case, the individual nanowires are in each case joined to the substrate layer individually. The flat sides of the flat mat-like nanowire structural element are defined by the surfaces of the template foil. As a result of the stable interconnection (mechanical integral joining at the nodes) of the nanowires, it is accordingly also possible to produce a nanowire network without any cover layers.

In order to obtain a sufficient nanowire density and stability of the nanowire network, the ion irradiation is carried out with an ion beam intensity which is sufficiently high enough that a sufficiently large number of intersecting nanopores at the nodes overlap, such that the intersecting nanowires merge together at enough nodes of the interconnected network. The intensity of the ion beam, or more precisely, the surface density (number of ions per surface unit) for each irradiation direction ideally should be at least $1 \times 10^7$ ions/cm$^2$, preferably, at least $5 \times 10^7$ ions/cm$^2$, and particularly preferred is at the rate of $5 \times 10^8$ ions/cm$^2$. The intensity of the ion beam should at least be high enough that a network is formed in which in the middle at least one node, in particular even more nodes, for each nanowire is/are generated. The nodes of the intersecting nanowires thereby, are between the ends of the nanowires, and due to the stochastic distribution of the ions during the irradiation are at different points along the length of the nanowires for each nanowire.

One advantage of the invention, among others, is that a nanowire network can be generated which is open on at least four sides, or at least five sides, or even on all sides (like a sponge) and is still stable and for the most part freestanding. The nanowire network forms thereby, in particular, a stable, or respectively, freestanding nanowire structural element. After complete removal of the template foil, an accordingly structurally stable hollow chamber-like structural component with a nanowire network structure remains.

These nanowire structural elements having a nanowire network open on all sides or merely closed by the substrate layer on one side or nanowire structural elements closed on two flat sides are excellently suited for use as, for example microreactor components, in particular as microcatalyzer components for heterogeneous catalysis. Furthermore, the nanowire structural element has a high level of long term stability as the nanowires are firmly anchored at numerous nodes to each other, and are not, for example, lying loosely in a microchannel. Even if the individual nodes should disconnect, the number of the remaining nodes is still sufficient to ensure the stability of the network.

The nanowires are preferably pulsed depositioned. The pulsed deposition has at least the following alternatives:

1) The deposition is carried out using pulsed deposition, i.e. deposition pulses alternating with deposition free diffusion periods.
2) The deposition is carried out by means of reversed pulse deposition, i.e. deposition pulses alternating with anodic counter-pulses.

Both alternatives have the advantage that in the breaks between the deposition pulses, ions in the electrolyte solution can re-diffuse in the nanopores, which leads to a uniform development of the nanowires.

The cathode layer can be generated by means of a known coating process, which is suited for application of a conductive, e.g. metallic, layer (e.g. vaporization, PVD, sputtering etc.). The cathode layer can be generated thereby in a single layer. Ideally however, the cathode layer is generated in at least two layers, wherein the first partial layer is applied through deposition, e.g. by means of PVD, sputtering, or vaporization and said first partial layer is then reinforced with a second partial layer by means of electrochemical deposition of another material, e.g. copper on gold.

The result of the production process described above is, accordingly, a nanowire structural element with a hollow chamber-like structure containing an array of numerous intersecting or angled nanowires which are merged together at numerous nodes. Merged, in this case, means that the nanowires are integrally joined to each other at an atomic/molecular level by means of the electrochemical deposition. The meshed nanowire network is therefore a unified developed system of matter from electrochemically depositioned material.

Interconnected open spaces exist between the nanowires in the nanowire network. The hollow chamber-like structure formed by the nanowire network is accordingly open celled, such that a fluid can be fed through the open cell hollow chamber-like structure in order to interact with the cylindrical surfaces of the nanowires which form a large surface area.

By means of the production process, there are however further certain structural properties of the constructed nanowire structural element. Because the nanowires, or respectively, the nanowire network are/is generated from electrochemical deposition materials, they can have a specific crystal structure which, for example, can be examined by means of X-ray diffraction. In this manner, based on the crystal structure, it is possible to determine whether the nanowire network was produced using the described process.

The diameter of the nanowires is preferably less than or equal to 2,000 nm, particularly preferably less than or equal to 500 nm, or respectively less than or equal to 100 nm. It currently seems possible to produced diameters as small as 10 nm or even less.

A larger aspect ratio allows for the production of a larger active surface area of the nanowire structural element. The aspect ratio of the nanowires is therefore ideally greater than or equal to 1:50, particularly preferred is greater than or equal to 1:100. It is also preferable that the average distance between the nanowires is greater than the average diameter of the nanowires.

The thickness of the nanowire structural element is defined by the thickness of the template foil. Due to the flatness of the template foil, the nanowire structural element is preferably also flat, or in the form of a thin mat. The thickness of the nanowire network is ideally less than or equal to 200 µm, particularly preferred is less than or equal to 50 µm. The dimensions in the two planes perpendicular to the thickness plane can amount to many times this. It is, for example, possible to produce a nanowire network of this type with a surface of 0.5 cm$^2$.

The surface density of the number of nanowires corresponds basically to the irradiation density (ions/cm²) is equally a measure for the active surface area. The surface density of the number of nanowires is ideally greater than or equal to n/F=10⁷ cm⁻², particularly preferred is greater than or equal to n/F=10⁸ cm⁻².

As a specific size for the active surface area of the nanowire structural element, the geometric specific surface of the nanowires per area of the nanostructure element and per length of the nanowires may be used. Accordingly, this geometrically specific surface area $A_v$ is:

$$A_v = \pi \cdot \frac{nD}{F\cos\alpha}$$

Wherein D is the average diameter of the nanowire and n/F is the surface density of the nanowires and $\alpha$ is the average angle of the nanowire to the surface plane of the template foil.

The geometrically specific surface area $A_v$ for each surface is determined by the total number of nanowires and should be at least 1 mm²/(cm² μm); larger values however are preferred, specifically where $A_v$ is greater than or equal to 5 mm²/(cm² μm), greater than or equal to 20 mm²/(cm² μm) or even greater than or equal to 100 mm²/(cm² μm). Where applicable, values of up to 1000 mm²/(cm² μm) may even be obtained.

In the production of the nanowires with the reversed pulse process, the nanowires have a distinct <100> texture, or respectively, a crystalline structure. With certain metals such as, for example, gold, it may be advantageous to create the smallest crystallite possible. For this a crystallite size of less than or equal 4 nm is preferred, wherein in general an average crystallite size of less than or equal to 10 nm may be advantageous.

Due to the crystalline texture, the actual size of the surface area, particularly the active surface area, is larger than the geometrically specific surface area $A_v$, which is based on the smooth cylindrical surface area, ideally by a factor of around 4-5.

A particularly preferred field of application for the nanowire structural elements produced according to the invention is heterogenic catalysis. This means one or more components serve as catalytic components, particularly for microcatalyzers.

A microcatalyzer ideally contains a microstructured channel system with a fluid intake and a fluid discharge and at least one nanowire structural element as a catalyzer element between the fluid intake and the fluid discharge, in order that fluid may be introduced by means of the fluid intake to the hollow chamber-like structure between the two cover layers, fed through the spaces between the nanowires and then removed by means of the discharge from the hollow chamber-like structure. In this manner, the two-dimensional open cell hollow chamber-like structure of the nanowire structural element forms the catalytic reaction volumes and the cylindrical surfaces of the nanowire form the catalytically active surface area which interacts with the fluid within the hollow chamber-like structure. Ideally, due to deposition, the nanowires are formed significantly (entirely of the same material) of, for example, platinum, in order that the catalytic element is a fully catalytic element.

Even when, due to the particular stability of the nanowire network, it is not actually necessary to apply cover layers to both sides of the nanowire structural element, this possibility should not be eliminated if it is desired, as, for example, in the following: the electrochemical deposition procedure of the nanowires is carried out at least until caps have formed on the second side of the template foil, and said caps merge to form a second closed cover layer on the side opposite the cathode layer. This surface covering cover layer increases in thickness in correlation to the length of time of the deposition. Accordingly, the electrochemical deposition procedure used to form the nanowires can be carried out long enough that the second cover layer in the form of a sufficiently thick, stable surface covering layer has formed. The nanowires are firmly joined in this case at both ends with the respective cover layers as a result of the electrochemical deposition. The cover layers may be, if desired, reinforced and completed as well, however, in a separate second, subsequent deposition procedure. The separate second deposition procedure can also be an electrochemical deposition, but can also consist of a coating process, such as PVD processes, vaporization or sputtering. Even when the separate deposition procedure is an electrochemical deposition, a different material may be used for the second partial layer than that used for the nanowires and the caps. It has been shown to be particularly beneficial if the nanowires and the caps are generated using a pulsed electrochemical deposition and the second partial layer is depositioned electrochemically using a direct current process. In particular, the nanowires and where applicable, the caps, are generated, using a reversed pulse deposition, from a metallic compound. For example, it has been shown to be beneficial to produce the nanowires and, if applicable, the caps, using reversed pulse deposition, from platinum and to produce the second partial layer from copper using direct current deposition. In this manner, the deposition procedure and the material costs can be reduced. The thickness of the substrate layer and the cover layer is ideally, in each case, less than 10 μm, e.g. approx. 5 μm to 10 μm.

A sensor element can be constructed from individual nanowire structural elements. The sensor element is suited, or intended, for use, for example, in measuring gas flow or temperature. Furthermore, the sensor element may be used as a movement sensor. The sensor element contains: at least one measuring device, which has a first nanowire structural element and a second nanowire structural element, wherein in each case, the nanowire elements have a first substrate layer and a second substrate layer for making contact with the respective nanowire structural elements. A "heat-able/warm-able element" is located between the nanowire structural elements. The heating results, for example, from application of voltage to the element, which, for example, may be a heat-able microwire. For this it is preferable that each nanowire structural element be connected individually. If a gas is fed through the sensor element, said gas is heated by the heated element, and in turn heats the nanowire structural element located behind the element, wherein a change in the resistance of the sensor element results or is induced. In this manner, the change in resistance is a measure of the gas flow through the sensor element. The change in resistance can also be a measure for the temperature change resulting from the gas flow. If the sensor element is moved, the change in resistance indicates a change in position. For this, the gas first passes through the first nanowire structural element, then the heat-able element and then the second nanowire structural element. The sensor element may be, for example, produced using a mask during the irradiation of the template used, in other words, using a process in accordance with claim 5.

In the following, the invention will be explained in detail using the embodiment examples and in reference to the illustrations, wherein identical and similar elements have the same reference symbols in part and the characteristics of different embodiments, particularly the procedures with and without radiation masks, can be combined with each other.

SHORT DESCRIPTION OF THE ILLUSTRATIONS

They show:

FIG. 1 An overview of the production of a nanowire structural element with a nanowire network.

Figure 2:
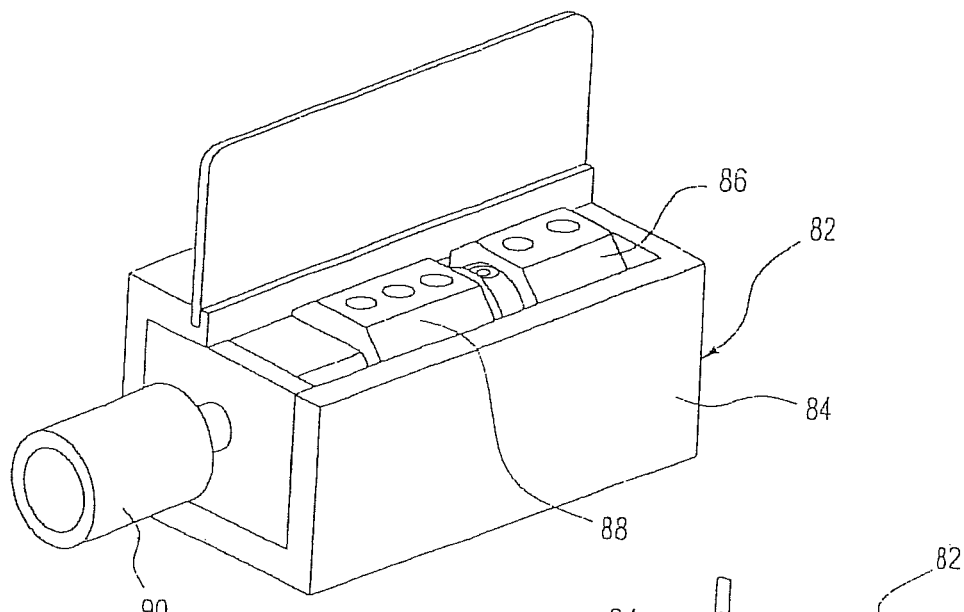

FIG. 2 A three-dimensional presentation of the deposition device used for electrochemical deposition.

Figure 3:
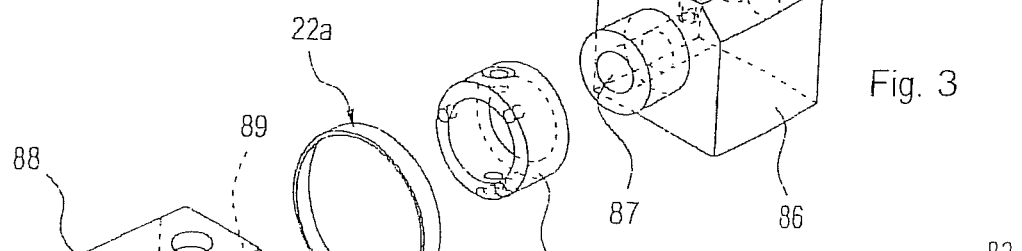

FIG. 3 A three-dimensional transparent exploded view of the deposition device for the deposition of the cathode layer.

Figure 4:
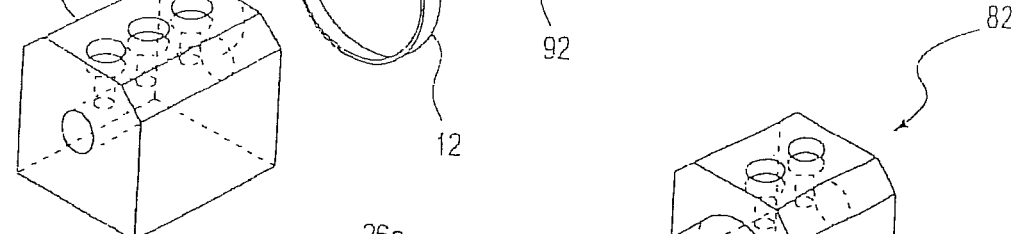

FIG. 4 A three-dimensional transparent exploded view of the deposition device for the deposition of the nanowires and, where applicable, a cover layer.

Figure 5:
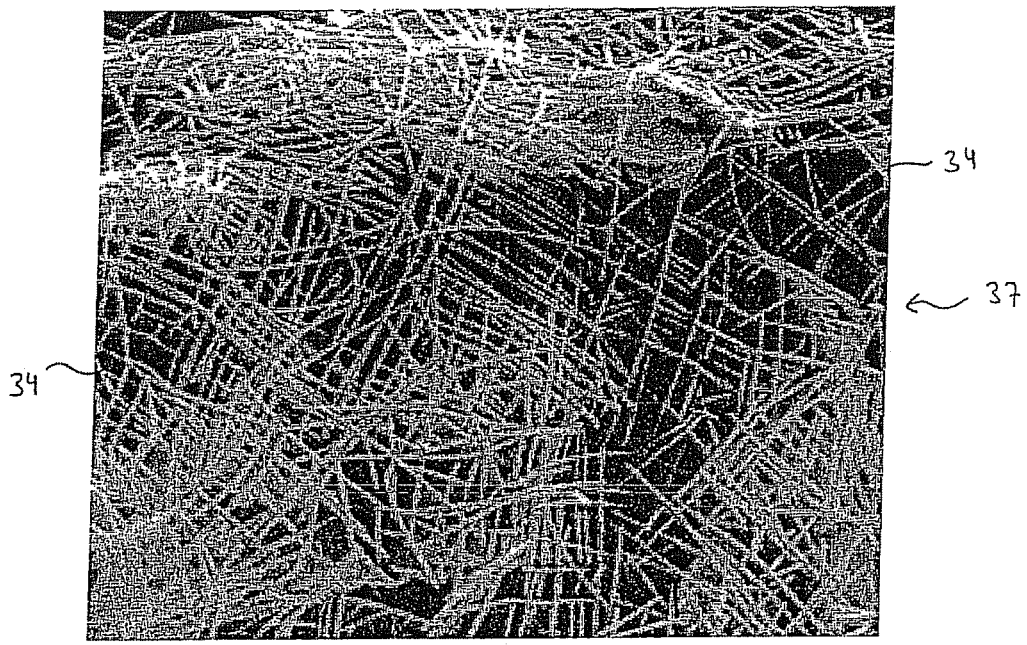

FIG. 5 An SEM image of a nanowire structural element with a nanowire network.

Figure 6:
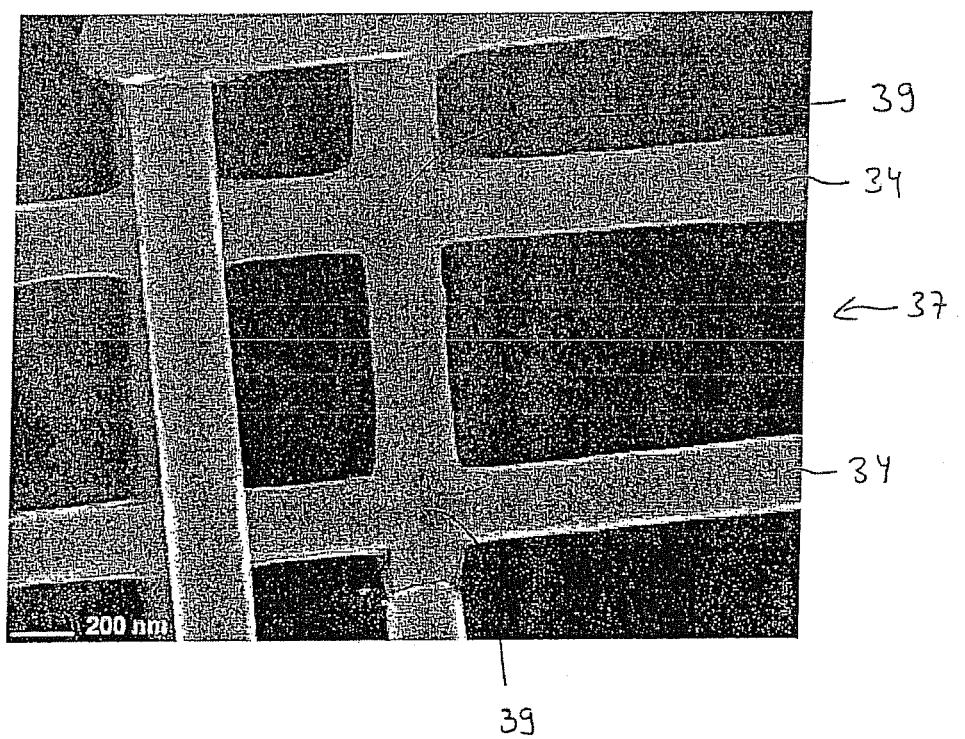

FIG. 6 An SEM image of the nanowire structural element from FIG. 5, significantly enlarged.

Figure 7:
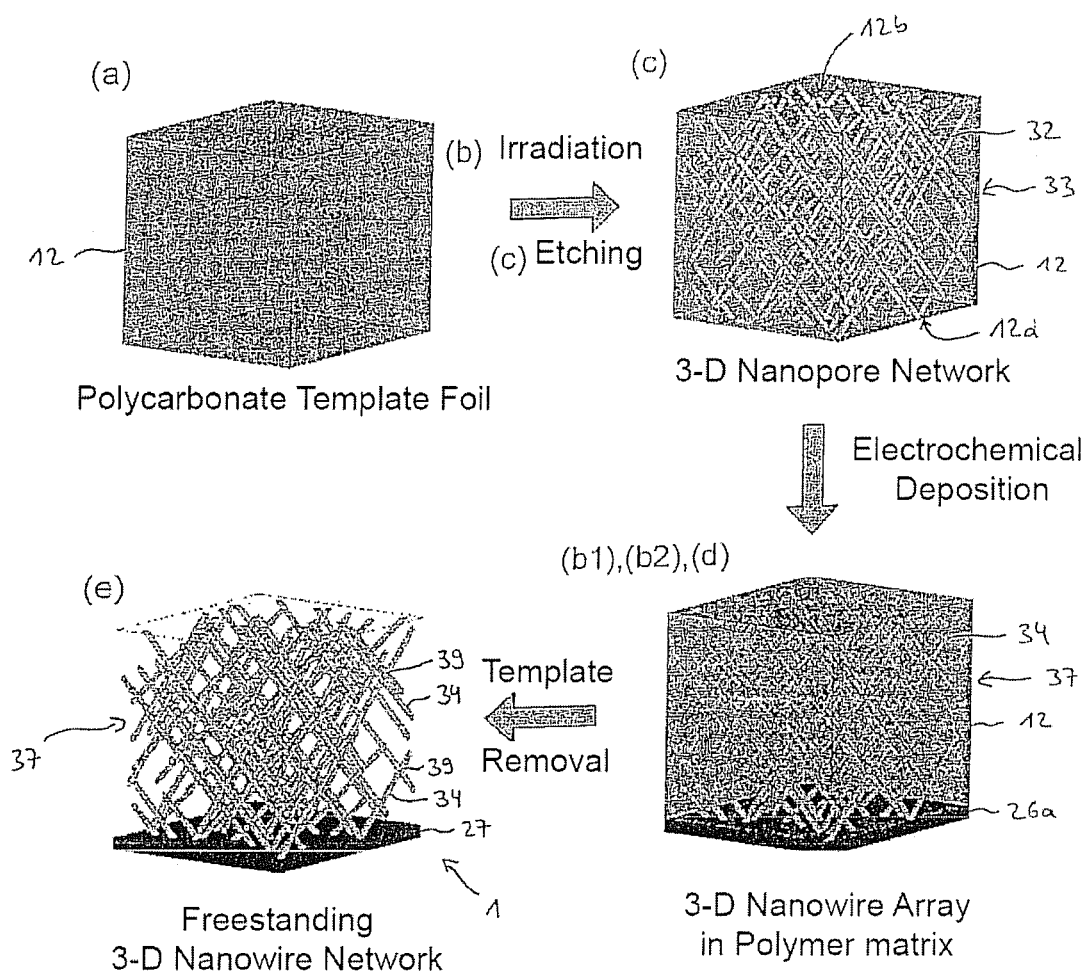

FIG. 7 A schematic overview of the production of a nanowire structural element with a three-dimensional (3-D) nanowire network.

Figure 8:
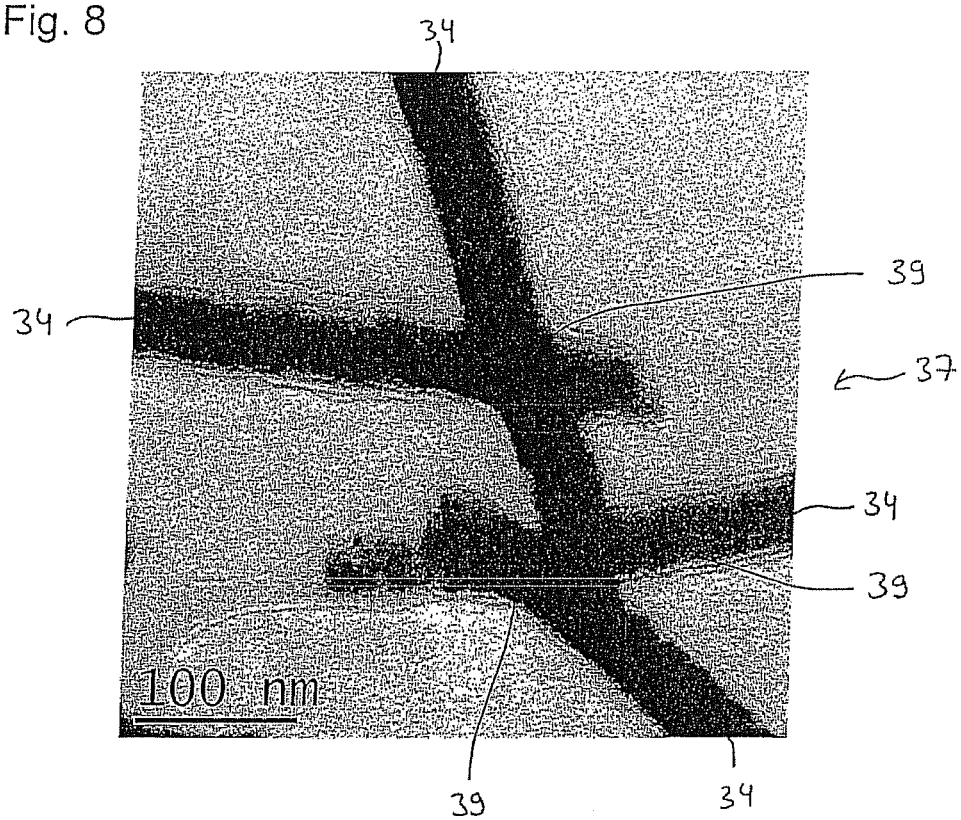

FIG. 8 A TEM image of a nanowire structural element open at two sides and closed at two sides with a nanowire array of platinum nanowires.

Figure 9:
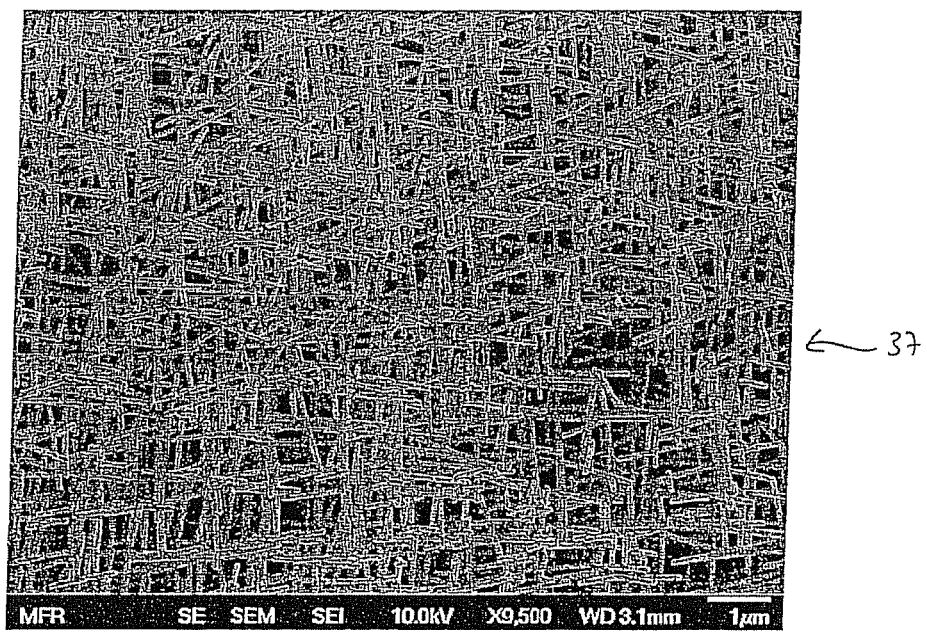

FIG. 9 An SEM image of the three-dimensional nanowire network from FIG. 8 slightly enlarged.

Figure 10:
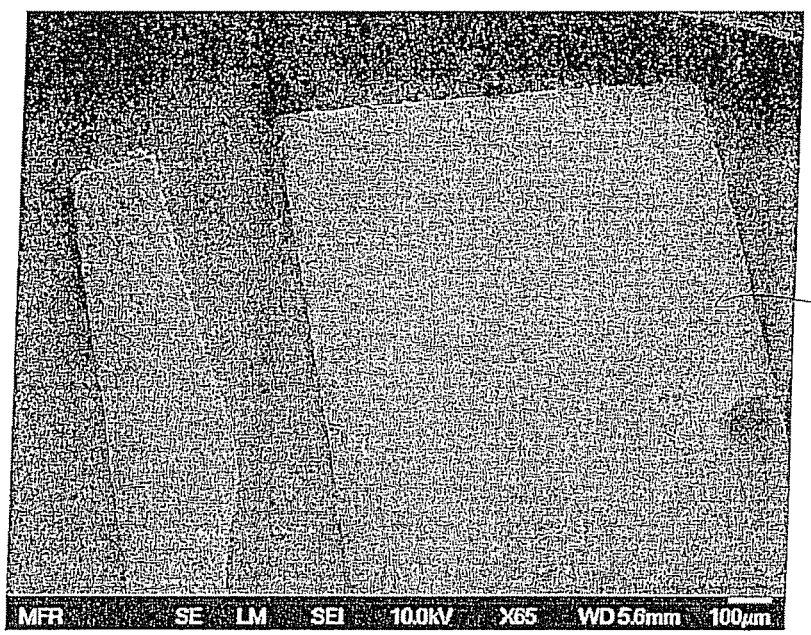

FIG. 10 An SEM image of the three-dimensional nanowire network from FIGS. 8 and 9 enlarged to a lesser degree.

Figure 11:
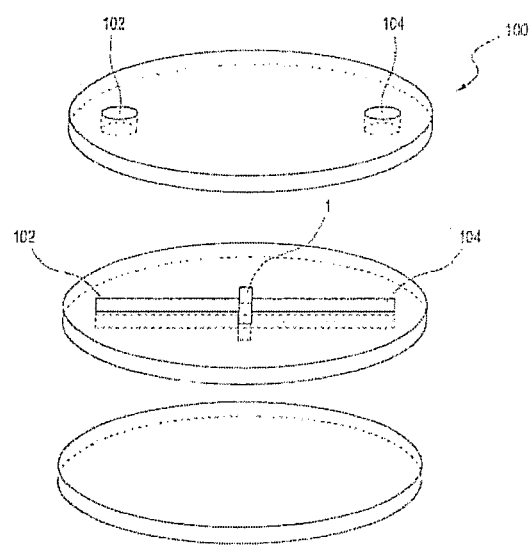

FIG. 11 A schematic exploded view of a microreactor with the nanowire structural element for use in flow operations.

Figure 12:
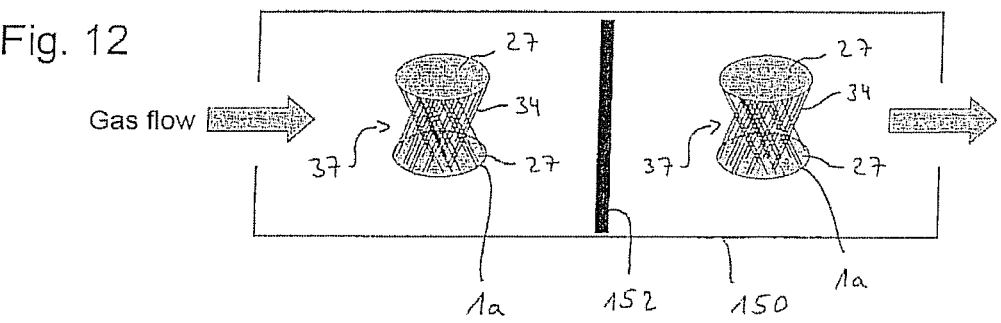

FIG. 12 A schematic presentation of a sensor element with two nanowire structural elements.

DETAILED DESCRIPTION OF THE INVENTION

Overview of the Production Process

The production of nanowire structural elements is based on a template based process. The partial steps of the process are schematically presented in FIG. 1 as follows:
(a) Preparation of the template foil,
(b) Irradiation with ions,
(b1) Application of a gold layer,
(b2) Electrochemical reinforcement of the gold layer (optional),
(c) Etching of the ion tracks to form nanopores,
(d) Deposition of the nanowires in the nanopores,
(d1) Removal of the cathode layer (optional),
(e) Dissolving and removal of the template foil.

Ideally, the process steps are carried out in the order shown in FIG. 1, i.e. (a), (b), (b1), (b2), (c), (d), (d1), (e). It is, however, basically possible to use a different sequence, such as, to etch from two sides and subsequently to then first to apply the cathode layer partial step ((c) before (b1) and (b2)) (see, e.g., FIG. 7).

In accordance with FIG. 1 (b), first a template foil 12 is bombarded with ions 14, wherein latent ion tracks 16 are generated in the substance of the template foil 12 along the trajectory (b1). The template foil 12 is a polymer foil in this example, specifically, a polycarbonate foil. A special feature of the process described here consists of the fact that the template foil is irradiated with ions from two angles in this example. In this example, the template foil is irradiated once at an angle of +45° to the surface of the template foil, and once at −45°, such that the latent tracks and later the intersecting nanopores, or respectively, intersecting nanowires run at an angle of 90° to each other. It is to be understood that other angles may also be used.

For successive irradiation of the template foil 12 at different angles, the template foil 12 is first positioned in an appropriate irradiation tube at a first angle to the direction of the ion beam, for example in the synchrotron of the GSI, and irradiated with a predetermined first ion surface density. Subsequently the template foil 12 is tilted in relation to the beam direction and irradiated with a second predetermined ion surface density. Should it be the case that nanowires are to be generated at different angles, the process is repeated until the angles have been obtained. The density of the ions, or respectively, the surface density necessary for a specific surface density of nanowires is calculated in advance and determined. The irradiation is then carried out with this predetermined ion surface density. To produce a 3-D network as explained below, a template foil 12 positioned at a polar angle to the beam axis is rotated on the beam axis to the azimuth angle.

Subsequently, on the first side 12a of the template foil 12, a thin, conductive metallic layer 22a, e.g. gold, is sputtered onto said (b1), forming a first partial layer. Subsequently, the first partial layer 22a is reinforced electrochemically with a second partial layer 24a thus forming the cathode layer 26a (b2), which later serves as a cathode for nanowire deposition (d). For the electrochemical deposition of the second partial layer 24a, the template foil 12 is mounted in the deposition device 82 shown in FIGS. 2-4.

Subsequently, the template foil 12 coated on one side is then removed from the deposition device 82, and the latent ion tracks 16 are chemically etched, wherein the continuous intersecting channels are created. These channels are referred to as nanopores and due to their different directions in the template foil 12, form intersecting and interconnected nanopores 32. Alternatively, the etching process may also be carried out in the deposition device 82, in that the etching solution is placed in the appropriate cell 88, and the repeated insertions are not necessary. The diameter of the nanopores 32 can be controlled by controlling the etching time period (c).

Following this, the template foil 12 prepared in this manner, permeated with the intersecting network 33 of nanopores 32, is placed again in the deposition device 82, and in a second electrochemical process, the desired metal for the formation of a network 37 of nanowires 34 in the nanopores 32 is electrochemically depositioned (d). In this example, platinum is depositioned in the nanopores, such that the nanowires 34, or respectively, the nanowire network 37, consist(s) of platinum. This platinum nanowire network 37 forms a catalytic active network due to the catalytic active surface of the platinum nanowires 34.

After the deposition of the nanowires, or respectively, the generation of the nanowire network 37 in the template foil 12, the cathode layer 26a may be removed if desired (d1). The removal of the cathode layer 26a is ideally carried out before the template foil is dissolved and removed. The gold cathode layer used in this example can be readily removed from the platinum nanowires. The cathode layer 26a can, however, remain on the template foil 12, and after the dissolving and removal of the template foil, forms a substrate layer 27, on which the nanowire network 37 is positioned and firmly joined (see FIG. 7 in the following).

Finally, the polymer foil 12 is dissolved in an organic solvent suited to this purpose (e). The nanowire structural element 1 produced hereby in accordance with the invention is shown in FIG. 1 (e).

The nanowire structural element 1 contains or consists of a nanowire array 35 of intersecting, interconnected nanowires 34, which form an integrally meshed nanowire network 37. The network 37 displays a certain stability due to the meshed structure of the merged together nanowires, even without cover layers, or, in other words, open on all sides, even when cover layers of this typed, e.g. on one side (substrate layer 27) or on both sides to form a sandwich structured are not excluded as a possibility.

The template based method has the advantage that many of the parameters can be specifically manipulated. The length of the nanowires 34 is determined by the thickness of the template 12 used and ideally is 10-200 μm, particularly preferred is circa 50 μm+50%. The surface density of the nanowires 34 is determined by the irradiation. The minimal surface density of the ion irradiation, and thereby the nanopores, should be selected such that a sufficient portion of the nanowires 34 can merge together. In this regard, a preferred surface density for the production of the array is ideally between approx. $1 \times 10^7$ cm$^2$ and $1 \times 10^9$ cm$^2$. The diameter D of the nanowires 34 is determined by the time period of the etching and may be from ca. 20 nm to 2000 nm. The aspect ratio may have values of up to 1000.

Possible materials for the nanowires are electroconductive materials, particularly metals or metallic compounds which are suited to electrochemical deposition. Experience has been made with the following metals which have been proven suitable: Cu, Au, Bi, Pt, Ag, Cu, Cu/Co multilayer, $Bi_2Te_3$.

On the one hand a large number of nanowires 34 with small diameters D is desired, in order to obtain a large active surface area, and on the other hand a good mechanical stability should be obtained. The optimization of this depends on the material used and is adjusted to the needs accordingly.

For nanowire structural elements 1 with platinum nanowires 34, a stable construction is produced with $10^8$ wires per cm$^2$ having a diameter of 250 nm and a length of 30 μm. The aspect ratio here is 120. Such nanowire structural elements are suited, for example, for use as catalytic elements due to the catalytic characteristics of for example platinum of the other elements contained therein.

Example 1

For the production of a nanowire structural element 1, a 30 μm thick circular shaped (r=1.5 cm) polycarbonate foil 12 (Macrofol®) irradiated with heavy ions 14 having an energy of 11.1 MeV/u and at two angles (+45°, −45° each having a fluence of $5 \times 10^8$ ions/cm$^2$ is used. Prior to the application of the conductive metallic layer 22a, each side of the polymer foil 12 is irradiated for one hour with UV light, in order to increase the selectivity of the etching along the tracks 16.

A gold layer 22a is sputtered onto the first side 12a of the polymer foil 12, having a thickness of ca. 30 nm (b1). This is reinforced by a potentiostatic deposition of copper from a $CuSO_4$ based electrolyte solution (Cupatierbad, Riedel) with a voltage of U=−500 mV, wherein a copper rod electrode serves as the anode (partial step 24a) (b2). The deposition is stopped after 30 minutes, at which point the copper layer 24a is approx. 10 μm thick. Subsequently, etching is carried out from the untreated side 12b of the template foil 12 at 60° C. with an NaOH solution (6 M) for 25 minutes and thoroughly rinsed with deionized water, to remove residual etching solution. At this point, the nanoporous template foil 12 is mounted in the deposition device 82.

The deposition of nanowires 34 is carried out at 65° C. with alkaline Pt electrolytes (Pt—OH bath, Metakem). To generate the nanowires 34, the process of the reversed pulse deposition is used in order to compensate for the slow diffusion driven transportation in the nanopores 32, and to obtain uniform development of nanowires 34. Following a deposition pulse of U=−1.3 V for 4 seconds, there is an anodic pulse for 1 second at U=+0.4 V. After a few tens of minutes, the deposition is stopped, and the development is checked. At this point, the nanowires 34 have developed sufficiently to merge together in the nanopores.

Finally, the template foil is removed, wherein the entire nanowire structural element 1 with the template foil 12 is placed in a container with 10 ml dichloromethane for several hours. In this example, the cathode layer remains as a substrate 27 on the nanowire array 35 and forms a component of the nanowire structural element 1. The solvent is replaced three times in order to fully remove residual polymers from the interior 38 of the nanowire array 35.

A nanowire structural element 1 produced in this manner may be seen in the scanning electron microscope images (SEM) in FIGS. 5 and 6. The nanowires 34 here have a diameter of approx. 150 nm. Because the irradiation is carried out at two angles it is referred to as 2-dimensional. Such a 2-D nanowire network structure may be seen therefore in FIGS. 5 and 6, which has been produced in a template that has been irradiated twice at different angles (+45°, −45°). It has formed a network which is relatively stable after removal of the polymer matrix, distributed on the substrate and joined to said.

The enlarged SEM image of a few nanowires 34 in FIG. 6 shows that the nanowires 34 have merged nicely at the nodes 39 and are thereby firmly joined and remain in place due to the predetermined radiation orientation of 90°. The nodes 39 where the nanowires 34 have merged together are predetermined by the intersections of the nanopores and are distributed at one or more places over the length of the nanowires 34, or between the ends of the nanowires 34.

Example 2

In reference to FIGS. 7-10, a further embodiment is produced. FIG. 7 shows schematically, and partially summarized the following partial steps of the process:
(a) Preparation of the template foil,
(b), (c) Irradiation and etching of the ion tracks to form nanopores,
(b1), (b2), (d) Generation of a cathode layer and deposition of the nanowires in the nanopores,
(e) Dissolving and removal of the template foil.

With reference to FIG. 7, the template foil or polymer membrane 12 is irradiated from more than two different directions. The irradiation is carried out in this example from four different directions, wherein the four irradiation directions are not in the same plane. With reference to perspective view shown in FIG. 7, radiation is applied in each case once from each of the four sides diagonally from above, and this being at a polar angle of 45° to the surface of the substrate and at azimuth angles of 0°, 90° 180° and 270°. The template foil 12 is therefore rotated at least three times during the irradiation.

When the template foil has been irradiated from at least three directions (in this example, four directions) which are not in a common plane, a three-dimensional nanopore network 33 (c) and subsequently a three-dimensional nanowire network 37 (d) and (e) can be produced. In other words, the irradiation directions and thereby the nanowires 34 lie in numerous (non-parallel) planes, which are at an angle to the template surfaces 12a, 12b. With a three-dimensional nanowire network 37 generated in this manner, the nanowires accordingly run in three non-parallel planes, thus forming a three-dimensional interconnected network structure. Expressed mathematically, the nanowires run along at least three non-parallel axes, which form at least two planes which in turn are not parallel. In this manner, the nanowires are not only connected to other nanowires in the same plane, but nanowires also exist which run at an angle to one of the planes formed by these nanowires. In other words, in the language of vector mathematics, it is possible with the at least three axes, or respectively, nanowire directions, to span a three-dimensional vector space. The, at least three, axes, or respectively, nanowire directions, are independent on a linear level. A three-dimensional interconnected nanowire network of this type is referred to here as a three-dimensional (3-D) nanowire network.

FIG. 8 shows a transmission electron microscope image (TEM) and FIG. 9 shows an SEM image with slight enlargement of a three-dimensional nanowire network 37 of this type, in which it may be seen that a mechanically stable, cohesive system of nanowires running at predefined angles has been formed, which remains erect to a large degree as a result of the predetermined orientation of the polymer matrix after the template has been removed, which can be seen particularly well in the SEM image in FIG. 9. The template 12 of the network 37 displayed here has been produced with 4 irradiations from four different linearly independent directions in each case with $5 \times 10^8$ ions/cm$^2$. The thickness of the nanowires here is approx. 50 nm.

Aggregation and loss of the active surface area is rarely observed, which means that excellent accessibility and ready catalyzer returns are obtained. The production process allows for a simple controlling of the network parameters by means of adjustment of the diameter of the wires, the integration density and the complexity (number of different nanowire directions) of the network. It is possible to produce very large nanowire networks 37 which are of several millimeters in two dimensions, as can be seen for example in FIG. 10. FIG. 10 shows an SEM image of the approx. 1 cm$^2$ nanowire structural element from FIG. 9. The entire nanowire structural element 1 is accordingly large on a macroscopic level. At the left edge of the image another somewhat smaller nanowire structural element may be seen. The Pt nanowire networks have a large catalytic active surface area, without a carrier substrate 27 being necessary, although this possibility is not excluded.

The nanowire structural element 1 in accordance with the invention accordingly has nanowires 34 connected to a network 37 wherein the network structure, in particular the 3-D network structures display the possibility for connecting, in a mechanically stable manner, micro- and even macroscopic structures. The stability is so great that they are suited for integration without cover layers on both sides, and as the case may be, even without a carrier substrate. Nearly all nanowires 34 are not only mechanically firmly connected, but also connected to each other in an electroconductive manner, wherein these structures have a large potential for use in electrocatalysis.

A Further Example Regarding the Deposition Parameters

In another example, the etching period is set at 18 minutes, resulting in nanowires 34 with a diameter of approx. 250 nm. The surface density (number for each surface) here is $10^8$ cm$^{-2}$. For the electrochemical deposition of the wires, the reversed pulse deposition is used again. A deposition pulse of $U_1=-1.4$ V for 40 ms is followed by a short counter-pulse of $U_1=-0.1$ V for 2 ms and a pulse interval of 100 ms at a voltage of $U=-0.4$ V, corresponding to a surplus voltage of approx. 0 V. This means that during the counter-pulse, the system is in a state of equilibrium.

Construction for the Electrochemical Deposition

With reference to the FIGS. 2-4 the electrochemical deposition of the nanowire array 35 consisting of numerous nanowires 34 is carried out using the deposition device 82, which shown in FIG. 2, in its entirety. It consists of a metal housing 84, in which the metal sled containing one of the two electrolysis cells 86, 88 can be inserted. Due to the good heat transfer properties of metal, it is possible to temper the deposition device by controlled external heating.

The electrolysis cells 86, 88 made of PCTFE have on their two facing sides, in each case, circular openings 87, 89 of the same size and can be pressed together firmly with a hand turned screw. A copper ring 92 between the two electrolysis cells 86, 88 serves as a cathode, or respectively, to establish contact with the first cover layer for the electrochemical deposition.

With reference to FIG. 3, for electrochemical reinforcement of the partial layer 22a, the ion track etched template foil 12 is mounted between the two electrolysis cells 86, 88 such that the partial layer 22a, in this case, the sputtered gold layer 22a, establishes good contact with the ring shaped copper electrode 92. On both sides of the copper ring used as a cathode, electrolytes are injected into the electrolysis cells. The electrochemical reinforcement of the gold layer 22a on the first cover layer 26a is carried out with a first anode 94, which is placed in the electrolysis cell 86 facing the partial layer 22a, and an external power source with a control device.

After removing the template foil 12 and etching the nanopores 32 outside of the deposition device 82, the template foil 12 is placed again in the deposition device 82.

With reference to FIG. 4, the template foil 12 which has been coated on one side and made porous is again placed in the deposition device 82 as in FIG. 3 for electrochemical deposition of the nanowires 34 and, where applicable, the completion of cover layer opposite the cathode layer 26a, such that the cover layer 26a makes contact with the ring electrode 92. At this point, deposition is carried out on the second side 12b of the template foil 12 with a second anode 96 located in the electrolysis cell 88 on the side away from the cathode layer 26a.

Examination of the Influence of the Electrochemical Deposition Conditions to the Development of the Nanowires With the pulsed deposition procedure for generating nanowires 34, a uniform length of the nanowires can be advantageously obtained at any point in time of the deposition. This can be explained, without claim to completeness and accuracy, in that the diffusion layers are kept relatively short in comparison to direct current deposition. In the intervals (equilibrium or counter-pulse) between the deposition pulses, metal ions in the nanopores 32 can re-diffuse such that on the entire electrode surface a nearly uniform concentration is obtained at the beginning of each deposition pulse, which results in a homogenous development. The diffusion layers barely overlap each other and irregularities in the surface are not enhanced.

Structural Characteristics of the Nanowires

In the framework of the invention the structural characteristics of the nanowires 34 made of different materials are also studied. With electrochemically depositioned material it is possible, for example, to control the size of the crystallite. This affects the mechanical stability, the thermal and electrical transference characteristics as well as the surface area and thereby also the catalytic activity. Many characteristics can thereby be strategically influenced.

In particular, the structure of the nanowires 34 is studied using X-ray diffraction. For this, the texture as a function of the electrochemical deposition is analyzed.

Pt nanowires 34 produced using direct current show a clear <100> texture. The texture coefficient $TC_{100}$ is 2.32, wherein the maximum value is 3. The size of the crystallite is determined by the half-width of the platinum signal by means of the Scherrer equation, and is 8 nm. For catalytic application, the smallest possible crystallite is desired. The value given here lies in the range of the nanoparticles otherwise used for catalysis. Based on this it may be assumed that the crystallite size can be reduced even more through modification of the electrochemical deposition conditions.

When studying nanowires 34 which are produced using pulsed deposition, one finds no specific texture. The intensity of the signals corresponds to those of polycrystalline platinum.

Finally, a sample produced using reversed pulse deposition, is studied. This also shows a clear <100> texture, wherein the texture coefficient $TC_{100}$ is 4.6. The crystallites display accordingly a preferred orientation, wherein the degree of the alignment is 83%. An alignment of at least 50% in this case is advantageous.

The characterization by means of X-ray diffraction of nanowires 34 produced using different means has shown that the deposition conditions have an effect on the texture. Therefore, the structure of the nanowire can be strategically influenced.

The surface of a nanowire 34 does not correspond to smooth surface of a cylinder, which is the basis for the calculation of the geometrical surface, but rather, it displays numerous recesses and swellings in its contour which significantly increases the surface area. The actual size of the surface area is therefore typically larger than the geometrical surface area, because, among other reasons, the crystallites from which the nanowires 34 are constructed are very small. In order to obtain a more precise idea of the surface area of the nanowire arrays 35, cyclovoltammetric measurements at 60° C. in 0.5 M $H_2SO_4$ are carried out for a potential range of 0-1,300 mV with a standard hydrogen electrode. From the load in which the adsorption of hydrogen is transmitted, it is possible, taking into account the capacitive currents, to calculate the surface area of the electrodes. The cyclovoltammetric examination of nanowire arrays shows that the actual surface area is greater than the geometrical surface area by a factor ranging from 4-5.

Applications

As a catalyzer it is possible to connect a series of numerous nanowire structural elements 1 according to the invention. Based on measurements, the nanowire structural element 1 is suited individually for application in microstructured systems having three-dimensional structures wherein the internal measurement is less than 1 mm and for the most part lies between ten and a few hundred micrometers.

FIG. 10 shows a schematic illustration of a microcatalyzer 100, in which a nanowire structural element 1 according to the invention is placed between a fluid intake 102 and a fluid discharge 104. It is conceivable that in a microcatalyzer 100 of this sort gas or fluid phase reactions can be carried out. For this purpose, a gas or fluid flow is directed under pressure through the microcatalyzer 100.

The nanowire structural element 1 produced according to the invention furthermore inherently contains an electric contact to all of the nanowires. As a result, a controlled voltage may be applied to the nanowires 34 thereby enabling Electrocatalytic processes. Furthermore, the component may be used as an amperometric sensor.

Production of Microelements using a Radiation Mask

In accordance with the invention, it is possible to create nanowire structural elements or nanowire arrays of very small sizes, in that the template foil 12, a polymer foil in this example, is irradiated with heavy ions through a corresponding mask. The mask, e.g. a perforated mask, which is already applied contains numerous openings or perforations, wherein each opening defines a future microelement 1a. The mask covers the template foil 12 during the irradiation, and latent ion tracks 16 are formed thereby, which are subsequently etched to form nanopores 32 only in the areas which are not covered by the mask, i.e. at the openings of the mask. The layout and the shape of the microelement 1a are determined therefore by the mask.

This process is specifically for the production of many very small nanowire structural elements, as stated, in the form of microelements. The microelements which may be produced in this manner consist of a 2- or 3-dimensional nanowire network 37 which may have a size of less than 500 μm, and particularly less than 100 μm, and where applicable, even less, to a size of only a few micrometers.

For example, a perforated mask for the ion irradiation with approximately 2,000 perforations is placed on the entire deposition surface of approximately 0.5 $cm^2$, such that approximately 2,000 microelements with nanowire arrays in islands in the template foil 12 can be created at once. After removal of the cathode layer, the microelements are separated from each other, and when the template foil has been dissolved and removed, are no longer attached to each other. It is, however, also possible to implement further steps, e.g. in order to generate cover layers for each individual microelement.

Because all nanowires 34 have electrical contact at both ends, the microelements with nanowire arrays are suited for production of miniaturized sensors. Due to the large number of wires, not only a high sensitivity but also a defect tolerance should result.

Further Applications

In particular, the microelements are suited for the production of sensor elements, e.g. for measuring gas flow, temperature and for use as movement sensors. In reference to FIG. 12, such a sensor 150 has at least one measuring unit with a first and second nanowire structural element 1a, wherein the nanowire structural element 1a in each case has a cover layer 27 on each side, wherein each of the two nanowire structural elements 1a establishes electrical contact by means of one or both of the cover layers 27, wherein the two nanowire structural elements 1a establish electrical contact separately. A heating element is located between the two nanowire structural elements, e.g. a microwire 152 which can be heated through application of voltage. Modification of the resistance of the sensor element 150 is used as a measure for the gas flow, the temperature or the change in movement.

It is clear to the person skilled in the art that the preceding descriptions of embodiments are to be understood as exemplary, and that the invention is not limited to said, but rather, can be varied in numerous ways, without abandoning the scope of the invention. In particular, the production of a microcatalyzer is only one of many uses for the nanowire structural element of the invention. Furthermore, it is clear that the characteristics are, regardless of whether they are presented in the description, the claims, the illustrations or otherwise, also define significant components of the invention, even if they are described in conjunction with other characteristics.

The invention claimed is:

1. A nanowire structural element that includes an array of numerous nanowires running in different directions and wherein the nanowires intersecting at numerous nodes have merged such that the nanowires are interconnected to form a network wherein the nanowires run along at least three predefined different directions within the network at 90° to each other, and wherein the at least three predefined different directions do not lie in a common plane, forming with the at least three predefined different directions a vector space, and the nanowires are interconnected in a three-dimensional manner and wherein the element is freestanding.

2. A nanowire structural element according claim 1, wherein the nanowire network is generated from electrochemically depositioned material.

3. A nanowire structural element according to claim 1, characterized in that it has a flat, mat-like shape.

4. A nanowire structural element according to claim 3, which does not have a cover layer on at least one side, and wherein the nanowire network is open on at least this one side.

5. A nanowire structural element according to claim 1 which furthermore contains a substrate layer with which the nanowire network is firmly joined.

6. A nanowire structural element according to claim 1, wherein the nanowires have a crystallite texture or a uniform crystalline structure.

7. A nanowire structural element according to claim 1, wherein the predefined different directions are irradiation-defined.

8. A nanowire structural element according to claim 1, wherein the nodes are predetermined.

9. A nanowire structural element according to claim 1, wherein the element has a stable hollow chamber-like structure.

10. A nanowire structural element that includes an array of numerous nanowires running in different directions and wherein the nanowires intersecting at numerous nodes have merged such that the nanowires are interconnected to form a network wherein all of the nanowires run along at least three predefined different directions within the network and wherein the at least three predefined different directions do not lie in a common plane, forming with the at least three predefined different directions a vector space, and the nanowires are interconnected in a three-dimensional manner and wherein the element is freestanding, wherein the at least three predefined directions at predefined angles includes a polar angle of 45 degrees and azimuth angles of 0 degrees, 120 degrees and 240 degrees.

11. A nanowire structural element according to claim 10, wherein the intersecting nanowires run at an angle of 90 degrees to each other.

12. A nanowire structural element according to claim 10, wherein the nanowires are greater than 50 nm in diameter.

* * * * *